United States Patent
Balmond et al.

(10) Patent No.: US 9,952,137 B2
(45) Date of Patent: Apr. 24, 2018

(54) CORROSION SENSOR HAVING DOUBLE-ENCAPSULATED WIRE CONNECTIONS AND MANUFACTURING METHOD FOR IT

(71) Applicant: BAE Systems plc, London (GB)

(72) Inventors: Mark David Balmond, Filton (GB);
Alexander Roy Parfitt, Filton (GB);
Gary David Panaghiston, Chelmsford (GB); Larry Brian Tween, Chelmsford (GB); Christopher Colin Figgures, Filton (GB)

(73) Assignee: BAE Systems plc, London (GB)

( * ) Notice: Subject to any disclaimer, the term of this patent is extended or adjusted under 35 U.S.C. 154(b) by 0 days.

(21) Appl. No.: 15/103,068

(22) PCT Filed: Nov. 20, 2014

(86) PCT No.: PCT/EP2014/075169
§ 371 (c)(1),
(2) Date: Jun. 9, 2016

(87) PCT Pub. No.: WO2015/086284
PCT Pub. Date: Jun. 18, 2015

(65) Prior Publication Data
US 2016/0313232 A1    Oct. 27, 2016

(30) Foreign Application Priority Data

Dec. 9, 2013  (EP) ..................................... 13275304
Dec. 9, 2013  (GB) .................................. 1321726.0

(51) Int. Cl.
*G01N 17/04*    (2006.01)
*B29C 45/14*    (2006.01)
(Continued)

(52) U.S. Cl.
CPC ....... *G01N 17/04* (2013.01); *B29C 45/14655* (2013.01); *B29C 45/14836* (2013.01);
(Continued)

(58) Field of Classification Search
CPC .................. G01N 17/04; G01N 27/041; B29C 45/14655; B29C 45/1671; B29C 45/34; B29C 45/00
(Continued)

(56) References Cited

U.S. PATENT DOCUMENTS 4,380,763 A    4/1983  Peart et al.
4,797,236 A *  1/1989  Kojima .................. B29C 45/00
                                                 264/102
(Continued)

FOREIGN PATENT DOCUMENTS

CN    203324154 U    12/2013
DE       256951 A1    5/1988
(Continued)

OTHER PUBLICATIONS

Translation of WO 2011249484.*
(Continued)

*Primary Examiner* — Jermele M Hollington
*Assistant Examiner* — Christopher McAndrew
(74) *Attorney, Agent, or Firm* — Maine Cernota & Rardin

(57) ABSTRACT

A sensor (1) and a method of manufacturing the sensor (1), the sensor (1) including a number of metallic strips (5,6,7) mounted on a non-conducting substrate (4) and a module (3) for forming electrical connections to the strips (5,6,7) whereby to enable communication between the strips (5,6,7) and monitoring equipment for the sensor (4), the module including a number of wire connections (16), the method including the steps of encapsulating the wire connections within a flexible chemical and heat resistant sealing com- (Continued)

Figure 1:
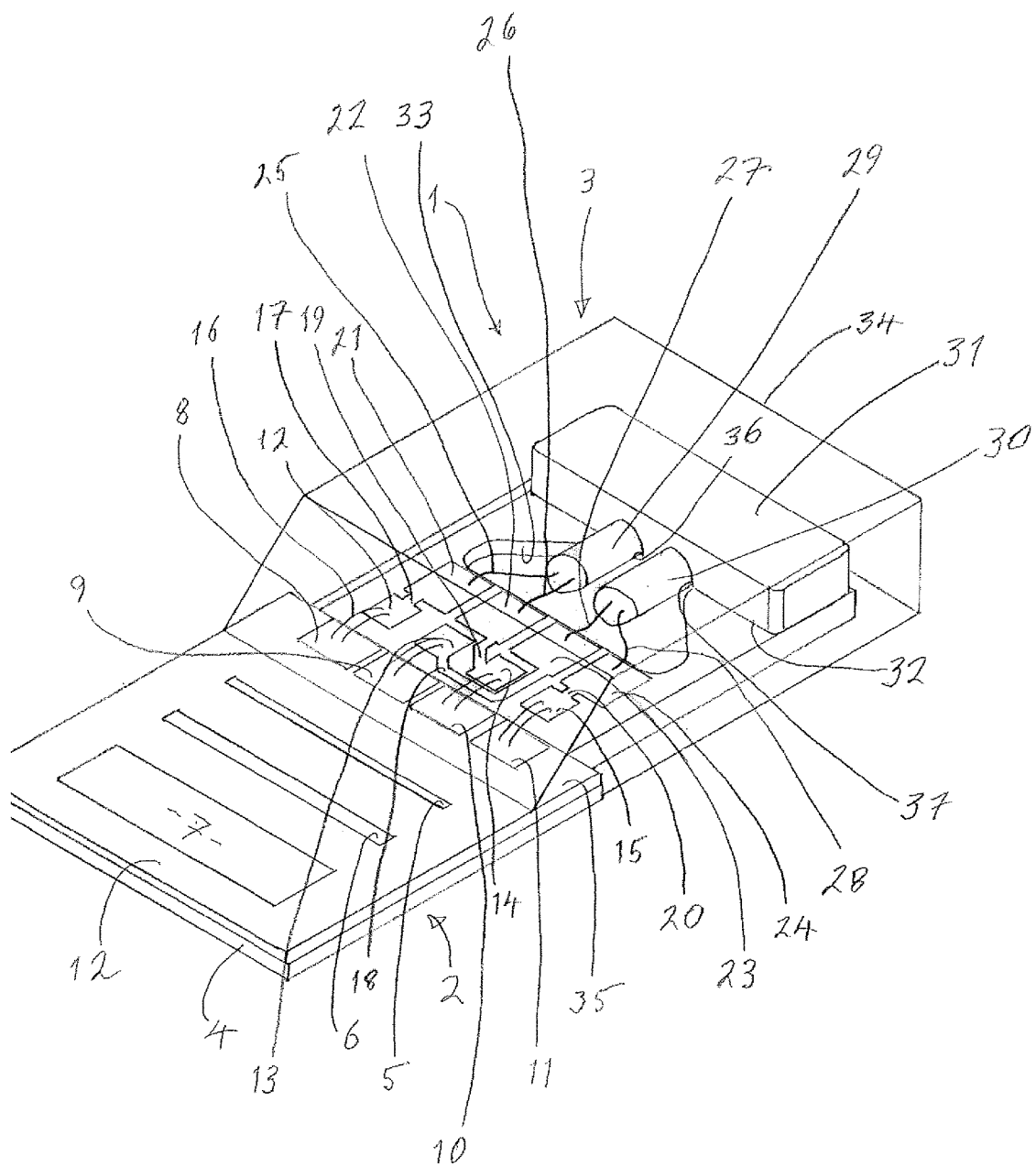

pound, and subsequently, encapsulating the flexible sealing compound within a second sealing compound (34) by an injection molding process.

14 Claims, 2 Drawing Sheets

(51) Int. Cl.
| | |
|---|---|
| B29C 45/16 | (2006.01) |
| B29C 45/34 | (2006.01) |
| B64D 45/00 | (2006.01) |
| G01N 27/04 | (2006.01) |
| B29K 79/00 | (2006.01) |
| B29K 305/02 | (2006.01) |
| B29L 31/34 | (2006.01) |

(52) U.S. Cl.
CPC .......... *B29C 45/1671* (2013.01); *B29C 45/34* (2013.01); *B64D 45/00* (2013.01); *G01N 27/041* (2013.01); *B29C 2045/14844* (2013.01); *B29C 2791/006* (2013.01); *B29K 2079/08* (2013.01); *B29K 2305/02* (2013.01); *B29L 2031/3481* (2013.01); *B64D 2045/0085* (2013.01); *H01L 2224/48091* (2013.01); *H01L 2224/48227* (2013.01)

(58) Field of Classification Search
USPC .......................................................... 324/700
See application file for complete search history.

(56) References Cited

U.S. PATENT DOCUMENTS

| | | | |
|---|---|---|---|
| 5,097,317 A | 3/1992 | Fujimoto et al. | |
| 5,127,433 A * | 7/1992 | Argyle .................. | G01N 17/00 116/206 |
| 5,181,536 A * | 1/1993 | Argyle .................. | G01N 17/00 116/206 |
| 5,253,674 A * | 10/1993 | Argyle .................. | G01N 17/00 116/206 |
| 5,286,357 A * | 2/1994 | Smart .................... | G01N 17/02 204/404 |
| 6,278,756 B1 * | 8/2001 | JinKim .................. | G01N 17/02 204/404 |
| 6,383,451 B1 | 5/2002 | Kim et al. | |
| 7,261,950 B2 * | 8/2007 | Fleming ............... | H05K 9/0094 174/350 |
| 7,351,479 B2 * | 4/2008 | Funkenbusch ....... | H05K 9/0094 174/51 |
| 2005/0247470 A1 * | 11/2005 | Fleming ............... | H05K 9/0094 174/394 |
| 2006/0006137 A1 | 1/2006 | Niblock | |
| 2006/0220189 A1 | 10/2006 | Sakamoto | |
| 2007/0144272 A1 | 6/2007 | Yu et al. | |
| 2008/0152743 A1 * | 6/2008 | Nguyen ................. | B29C 33/44 425/46 |
| 2008/0208283 A1 * | 8/2008 | Vetter .................. | A61N 1/0534 607/45 |
| 2009/0128169 A1 * | 5/2009 | Fay ........................ | G01N 17/04 324/700 |
| 2009/0195260 A1 * | 8/2009 | Bell ....................... | G01N 17/04 324/700 |
| 2010/0022713 A1 * | 1/2010 | Venkataraman ...... | B29C 7/0004 525/199 |
| 2010/0052704 A1 | 3/2010 | Fay et al. | |
| 2010/0090802 A1 * | 4/2010 | Nilsson .................. | G01N 17/04 340/10.1 |
| 2010/0126859 A1 | 5/2010 | Yang | |
| 2011/0187395 A1 * | 8/2011 | Morgan ................. | G01N 17/04 324/700 |
| 2012/0038377 A1 | 2/2012 | Hamann et al. | |
| 2012/0174396 A1 * | 7/2012 | Hefner .................. | G01N 17/04 29/874 |
| 2012/0176147 A1 * | 7/2012 | Hefner .................. | G01N 17/02 324/700 |
| 2012/0177811 A1 * | 7/2012 | Hefner .................. | G01N 17/04 427/9 |
| 2012/0223457 A1 * | 9/2012 | Hefner .................. | G01N 17/04 264/272.11 |
| 2013/0069676 A1 * | 3/2013 | Steinwandel ........ | G01N 17/043 324/700 |

FOREIGN PATENT DOCUMENTS

| | | |
|---|---|---|
| EP | 0346786 A2 | 12/1989 |
| EP | 0357802 A1 | 3/1990 |
| EP | 1923821 A1 | 5/2008 |
| GB | 2522114 A | 7/2016 |
| WO | 2011148441 A1 | 12/2011 |

OTHER PUBLICATIONS

Preliminary Report on Patentability for PCT Application No. PCT/2014/075169, dated Jun. 23, 2016, 9 pages.
PCT International Search Report and Written Opinion dated Dec. 19, 2014 of Patent Application No. PCT/EP2014/075169 filed Nov. 20, 2014.
European Search Report dated Jan. 6, 2014 of Patent Application No. 13275304.7 filed Dec. 9, 2013.
Great Britain Search Report dated Mar. 6, 2014 of Patent Application No. 1321726.0 filed Dec. 9, 2013.
Great Britain Search Report dated May 7, 2015 of Patent Application No. 1420633.8 filed Nov. 20, 2014.
Certificate of Grant dated Apr. 6, 2016 for Great Britain Patent Application No. 1420633.8, now Patent No. GB 2522114.
Great Britain Examination Report dated Jan. 20, 2016 for Patent Application No. 1420633.8 filed Nov. 20, 2014.
Response dated Jan. 27, 2016 to Great Britain Examination Report of Jan. 20, 2016 for Patent Application No. 1420633.8 filed Nov. 20, 2014.
Jennifer L Elster et al: "Corrosion Monitoring in Aging Aircraft Using Optical Fiber-Based Chemical Sensors", Fourth Joint DoD/FAA/NASA Conference on Aging Aircraft Proceedings, St. Louis, Missouri, pp. 13-20., Jan. 1, 2000, XP055094687, Retrieved from the internet: URL: http://tregoengineering.com/PDF_Papers/aging2000_corr_fo.pdf.
Estefania Abad et al: "4 Fabrication and Encapsulation Processes for Flexible Smart RFID Tags", Radio Frequency Identification Fundamentals and Applications Design Methods and Solutions, Jan. 1, 2010, XP055094696, Retrieved from the Internet: URL: http://www.intechopen.com/download/get/type/pdfs/id/8468.

* cited by examiner

CORROSION SENSOR HAVING DOUBLE-ENCAPSULATED WIRE CONNECTIONS AND MANUFACTURING METHOD FOR IT

This invention relates to the manufacture of sensors for detecting corrosion on a metallic material when the sensor is mounted on or adjacent the metallic material, in use.

Such corrosion sensors are often placed in inaccessible or difficult to access locations on movable structures such as aircraft, ships or other vehicles. Corrosion of metallic structures, particularly in corrosive environments such as on seagoing vessels or carrier-based aircraft, is an enormous financial problem for operators and can amount to billions of dollars per annum, as is the case, for example, for the US military. The use of such corrosion sensors, which can be used to signal various stages of corrosion of a structure on which they are mounted, can give the owner remote information on the state of corrosion of areas which are hard-to-access, are functionally critical or are highly numerous and would lead to excessive inspection time.

Corrosion is a problem which leads to high maintenance and repair overheads in many different industries. The paper "Naval Aviation Corrosion Challenges and Solutions", Dale L. Moore, Corrosion 2000, paper 00270 (NACE, Orlando, USA, 2000) describes the problem areas in aircraft component corrosion and classifies corrosion types found in the aircraft industry.

Looking now at the construction of the corrosion sensor, the sensor consists of a chip coupled with a connecting module containing electrical connections between the chip and external monitoring means. The electrical connections are housed in a weather-proof and corrosion-proof capsule, whereby to form the module. The basic sensor chip consists of a thin substrate, which may be of silicon, coated with a coating of an insulator such as silicon dioxide. The substrate may be flexible and may be of a material such as polyimide which may act as both substrate and insulator. Onto the insulator is deposited at least one layer of conducting material, such as aluminium alloy, which may be formed, using masking technology, into a single strip or into strips of different width. The thickness of the layer forming the strip or strips may be approximately 150 nm, so it will be appreciated that the sensor is potentially very fragile.

The circuitry is designed to communicate signals from the strip or strips, which reflect the occurrence of corrosion, to remote monitoring equipment.

The conducting strip or strips and connecting tracks are integrally formed on the substrate from a conducting material designed to be the same as or to mimic the corrodible material on which the sensor is to be mounted in use. An example of this conducting material would be aluminium alloy for use on aircraft. The chip is then usually painted. This paint may be the same paint as will be used to cover the corrodible material on which the sensor is to be mounted although, for "time of wetness" sensors for example, the chip would not generally be painted and may consist simply of a single area of thin film track on an insulating material. For ships and aircraft, the paint would be a paint containing a corrosion inhibitor and, although not essential, such chips are primarily designed to be used with paints containing a corrosion inhibitor.

For maritime applications, sensors are generally coated all over with paint. However, not all paint layers are present in all areas. Paint layers are selectively applied to different areas of the sensor in order that the difference in the rates of coating breakdown can be monitored individually for each paint layer, e.g. primer, undercoat & topcoat. Thin film metallic resistors are strategically positioned beneath the paint and, when coating breakdown occurs, the resistance of the underlying thin film resistors changes in the specific area, as they are no longer fully protected against corrosion. Such sensors may also be used for land vehicles.

For aircraft applications, the paint is generally applied all over the sensor chip save for the conducting strip, or strips, which are left bare. The relatively narrow width of the exposed strips is designed to represent paint flaws or other damage which may occur to the paintwork such as cracks, scratches, chips etc. If corrosion inhibitor paint is used, the inhibitor will leach out from the paint and spread over the bare strips. Depending upon the width of the strip, the leaching inhibitor will either fully or partially extend over the area of the strip and will therefore either fully or partially protect the strip from corrosion. For wider strips, the strip may be only partly protected by inhibitor and corrosion will then attack the strip almost immediately. The strip will therefore fail before other, narrower strips for which protection will last longer. In this way, the sensor will provide corrosion sensing with different sensitivities and with different lifetimes, depending upon strip width. Although, primarily aimed at aircraft applications, this type of sensor may also be used for other applications where appropriate, e.g. for certain types of land vehicle.

In operation, the sensor is affixed either to the structure being monitored for corrosion or adjacent to it and in a position subject to the same corrosive influence. The sensor is connected to monitoring equipment, usually remote, either directly by wires or via radio link or other remote connection means. It will be appreciated that many locations in which the sensor is to be mounted will suffer harsh environments and the sensor may be subject to twisting forces, vibration and of course corrosive influence. The sensor must therefore be robust in construction and the electrical circuitry must additionally be corrosion proof.

To date, such corrosion proofing has proved difficult, if not impossible, to achieve. The sensor has tended to flex and damage the strips or wires attached to the strips or their connections and the protection for the circuitry has thus proved inadequate. In addition, the connecting module has proved troublesome to manufacture, for reliable operation. In particular, faults in the sealant such as air bubbles have tended to form. Such air bubbles can lead to cracks forming in the sealant at high altitude where the atmospheric pressure is reduced. Such cracks can lead to destruction of the structural integrity of the sensor which may cause immediate failure of one or more electrical connections and/or may allow moisture to enter the sensor and corrosion to set in.

An improved potting method was required to encapsulate the pads and connections, to avoid the above difficulties. Only the pad area of the sensor chip needs to be encapsulated or "potted", the rest must be exposed to the environment and the fragile (thin film) sensor elements must remain perfectly clean until the sensor is installed. Standard potting techniques, for example encapsulation in epoxy resin, were not suitable for two reasons. Firstly, the surface of the sensor chip must be painted with a platform specific paint, e.g. aircraft paint, and there is no obvious way of ensuring a good seal between this painted surface and any standard potting compound. Secondly, there was no obvious way of using an aircraft sealant to form any intermediate seal between the paint and any standard potting compound.

The connecting module contains three series of connections, firstly, connections from a first set of pads on the chip, secondly, connections to a second set of pads and, thirdly, connections from a third set of pads to wires leading from the sensor.

The connecting pads on the chip are typically constructed using an aluminium alloy and these pads are extremely thin, of the order of 1 µm. Therefore, it has not been possible to solder wires to these pads. Instead, at least one further set of pads is provided, preferably two sets and preferably of copper. These further pads preferably comprise a set of printed input pads and a matched set of printed output pads. Each input pad is connected by a printed track to a matched output pad. Between each chip pad and its matched printed input pad there is connected, by ultrasonic wedge bonding, a series of very thin wires. To each output pad is connected, by soldering, a wire leading from the sensor.

It will be appreciated that the wire bonds and the thin wires themselves will be fragile. This is particularly the case because each thin wire loops upwardly from the surface of the chip pad and down again to the surface of its matched input pad. Breakage of these thin wires or their bonds, either during manufacture or during use of the sensor, has been common. Breakage during manufacture can occur when protective sealant or potting compound is applied to encapsulate all the connections. Breakage during use can occur owing to slight flexing of the sensor or due to moisture entering the sensor through, or alongside, the sealant or potting compound.

Further problems can occur with the wires leading from the sensor. The potting compound has proved inadequate to securely locate the wires with respect to the output pads and thus prevent fracture of the soldered connections.

The cable used for the sensors may need to be qualified for use on-board naval vessels & high altitude jet aircraft. The most suitable cables for such applications (and indeed the only qualified cables in existence for certain platforms) are PTFE coated and sealing to PTFE surfaces to potting compounds is known to be difficult.

Furthermore, in order to make volume production of the sensors viable and to enable sufficiently high quality potting, aircraft sealant would need to be injection moulded. Injection moulding of aircraft sealants has not been attempted, previously.

For all the above reasons it has so far not proved possible to manufacture a sensor of the above type which will operate reliably.

According to a first aspect of the present invention there is provided a method of manufacturing a corrosion sensor, the sensor including at least one metallic strip mounted on a non-conducting substrate and a module for forming electrical connections from external monitoring equipment to the at least one strip, the module including a number of wire connections, the method including the steps of encapsulating the wire connections within a flexible chemical and heat resistant sealing compound/adhesive, and subsequently, encapsulating the flexible sealing compound within a second sealing compound by an injection moulding process.

The flexible chemical and heat resistant sealing compound may be, for example, Raychem S1125 epoxy and the second sealing compound may be, for example, PR2001B2 two-part epoxy aircraft sealant, for use on aircraft.

The second sealing compound may be PR-2001 Class B. This is a two-part, epoxy cured Permapol® P-3.1 polythioether compound. It is a rapid cure, low odour, aircraft integral fuel tank sealant with a service temperature range from −62° C. to 160° C., with intermittent excursions up to 216° C. This compound is designed for fillet sealing of fuel tanks and other aircraft fuselage sealing The wire connections may be formed by first, second and third wire connections, respectively. The first and second wire connections may be made at pads on the chip and at a set of intermediate pads in the module, respectively, and the third wire connections may be made at a set of output pads in the module. The first and second wire connections may be made by ultrasonically bonding very fine wires, at first ends thereof, to the chip pads and, at second ends thereof, to the intermediate pads. The third wire connections may be made by soldering the output pads to output wires for the module.

The intermediate pads, the output pads and tracks interconnecting them together may be formed of copper topped with gold, with the pads and tracks being applied to the substrate of the sensor in a known manner.

Prior to the first encapsulation step, at least some of the wire connections may be manually coated with a preliminary sealing compound, for example, Dymax 9001, an ultraviolet-cured encapsulant, with Araldite 2014, a two-part epoxy adhesive, or with M-Coat D acrylic. Thus, for example, the Dymax or the Araldite may be used on the fine wires and ultrasonically bonded joints and the M-Coat D may be used on the soldered joints. Where appropriate, the preliminary sealing compound may be cured, for example, by ultra-violet radiation.

For simplicity and for strength of the sensor, the chip and the module may be mounted on a single substrate. This may be flexible or rigid, according to specific design requirements, and may be of printed circuit board material such as FR4. The chip may be glued into position on the substrate using an adhesive such as Araldite 2014, Marine.

Once the wires have been attached to the output pads, they may be clamped in position to the module to protect the soldered joints from any pushing, pulling or vibration forces acting on the wires.

Where the substrate is FR4 material, this same material may be suitably employed as a clamp to place over the wires leading from the sensor and may be fixed in position, for example by use of an adhesive applied between the substrate and the clamp. The clamp may be formed with wire feed-through passages to receive the wires as they pass from the output pads and exit the sensor unit.

Once the clamp has been applied, a flexible sealant such as Raychem S1125 flexible epoxy may be applied to all the wire connections and to the feed-through passages. The flexible sealant may be applied manually or may be injection moulded if the sensor is first placed in a suitable mould. This mould may of course be used to provide a desired external shape for the flexible sealant as well. Raychem S1125 is particularly suitable for sealing the wires to the substrate and the clamp at the feed-through passages, because this product has been found to seal effectively to any PTFE sleeve applied as covering for the wires. A further enhanced seal between the flexible sealant and the PTFE sleeve may be obtained by etching the PTFE sleeve with an etching product such as Tetra Etch before the flexible sealant is applied.

The mould, for the injection moulding step, may be connectible to a vacuum source at an outlet from the mould, whereby the vacuum may assist in evacuating the mould of any gas bubbles or voids in the mould sealant. The step of connecting at least one mould outlet to a vacuum source may comprise placing the injection mould in a vacuum chamber whereby to carry out the injection moulding step within a vacuum. It should be emphasised that placing the injection mould in a vacuum chamber enables the moulding within the mould to be subject to the vacuum for the whole time that injection moulding takes place, if required.

The moulding material or sealing compound may be supplied, for injection moulding, in an air-tight container such as an evacuated tube. The injection moulding step may be carried out by connecting the air-tight container to a mould inlet and forcing the sealing compound from the air-tight container into the mould. This step may be carried out, where the container is a tube, by compressing part of the tube whereby to reduce the volume inside the tube and thereby to expel the sealing compound from the tube.

Placing the mould in a vacuum chamber, prior to injection of the moulding compound, provides the necessary enhanced moulding conditions to give the required structural integrity to this highly specified component.

In the past, vacuum has traditionally been either (i) applied to evacuate a container, holding the moulding compound, prior to injection or (ii) applied after injection moulding has taken place and only once an upper portion of the mould had been removed, to allow a sufficient surface area of the moulded material to be exposed to the vacuum. It will be appreciated that removal of any part of the mould tool of an injection mould whilst the moulded material is still within the mould and is not fully set or cured may result in distortion of the surface of the moulded material from its intended shape. In the case of aircraft sealant, this will not self level, in the absence of the forming shape of the mould tool, and removal of any part of the mould tool surface tends to result in defects to the surface of the finished component.

This evacuation feature can be particularly important when the injected sealant is to be used at altitude when expansion of any gasses trapped within the moulded sealant can cause stress fractures in the sealant which may in turn lead to moisture entering the device and/or electrical breakdown.

Unlike in other applications, re-heating of the moulding compound cannot be safely undertaken in order to re-flow it. Such a process is not suitable when using an aircraft sealant as the moulding compound. Indeed, initial moulding cannot be carried out at elevated temperatures either, for the same reason. Here, in any event, the solder and initial encapsulants used for the sensor cannot take the temperatures required for a hot moulding process.

According to a second aspect of the present invention, there is provided a corrosion sensor including a number of metallic strips mounted on a non-conducting substrate and a module for forming electrical connections to the strips whereby to enable communication between the strips and monitoring equipment for the sensor, the module including a number of wire connections the wire connections being encapsulated within a flexible chemical and heat resistant sealing compound and the flexible sealing compound being encapsulated within an injection moulded second sealing compound of aircraft sealant.

According to a third aspect of the present invention, there is provided a corrosion sensor manufactured according to the method of the first aspect of the invention.

According to a fourth aspect of the present invention, there is provided an injection mould for the manufacture of a corrosion sensor according to the second aspect of the invention, the injection mould comprising a bed and first and second upper portions defining a mould cavity therewithin, the bed containing a hollowed out portion into which is placed the non-conducting substrate and the module unencapsulated by the injection moulded second sealing compound of aircraft sealant, and means to inject the aircraft sealant under pressure into the cavity through one or more injection ports.

The injection mould may have a vacuum source connected to one or more outlet ports of the mould and the vacuum source may comprise a vacuum chamber in which a remainder of the injection mould is housed.

Figure 2:
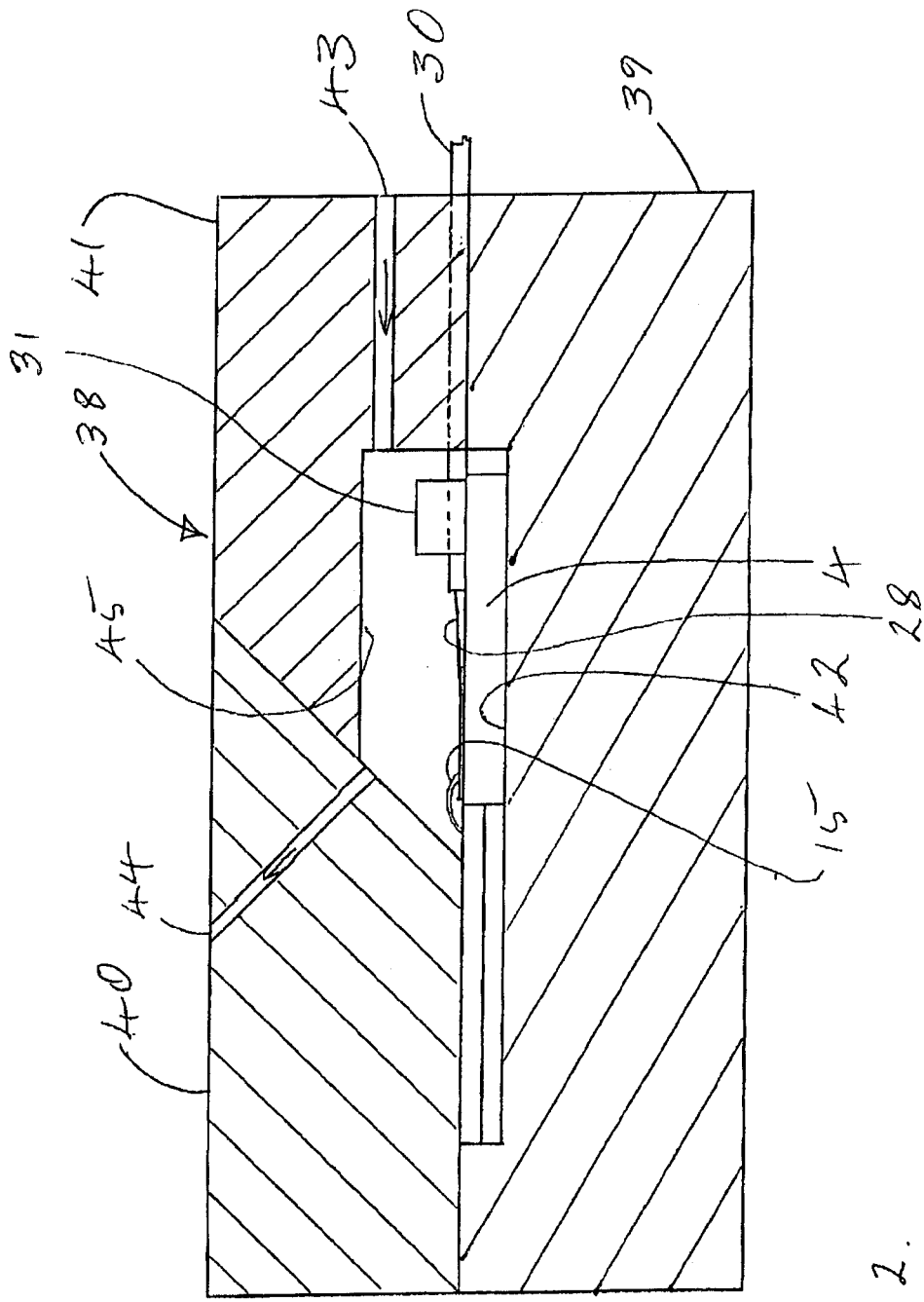

The invention will now be further described by way of example with reference to the accompanying drawings of which:

FIG. 1 is a ghosted three dimensional sketch of a sensor made according to the invention, and FIG. 2 is a cutaway side view of a mould for applying sealant to the sensor whereby to form the capsule thereof.

Referring to FIG. 1, a sensor 1 made according to the invention is shown. The sensor 1 comprises a chip portion 2 and a connecting module 3. Both the chip portion 2 and the module 3 are formed on a single rigid substrate 4 of FR4 printed circuit board material.

Referring initially to the chip portion 2, this consists of a substrate of silicon (not separately shown) on which is formed a thin layer of silicon dioxide (again not separately shown) which acts as an insulator. Onto the layer of silicon dioxide is deposited a double layer of aluminium alloy material. This layer appears in the drawing as strips 5, 6 and 7 and strip pads 8, 9, 10 and 11. Over the double layer of aluminium alloy is applied at least one layer of paint 12 which has gaps corresponding to the strips 5, 6 and 7 and the strip pads 8, 9, 10 and 11.

The paint 12 and the aluminium alloy will be selected to correspond as closely as practicable to those in use on the metallic painted material whose corrosion is to be monitored by the sensor. Where the paint contains corrosion inhibitor, this will leach out of the paint over the otherwise unprotected strips 5, 6 and 7. That part of the strip covered by the inhibitor will be protected from corrosion. If the inhibitor fails to reach right across the strip, however, such as for the widest strip 7, then corrosion of that strip will set in as soon as it becomes subject to corrosive influence. In a similar manner, once corrosion inhibitor has ceased to leach out of the paint onto the remaining strips, the strips will be left unprotected and corrosion will begin. With the strips shown, widest strip 7 will begin to corrode first, followed by the centre strip 6 and finally by the narrowest strip 5. The sensor thus enables measurement of corrosion at different sensitivities and over differing periods, using the sensor strips of differing widths.

Strip pads 8, 9, 10 and 11 are connected, under the paint, to strips 5, 6 and 7 such that the voltage or current from each strip can be measured separately.

Turning now to the connecting module 3, each strip pad 8, 9, 10 and 11 is connected to a corresponding intermediate pad 12, 13, 14 and 15 by very fine wires 16 ultrasonically wedge bonded at either end. The whole of the connecting module 3 is encapsulated in PR2001B2 aircraft sealant 34 which has been injection moulded around the connecting module 3 and an enclosed part 35 of the chip portion 2. It will be observed that the tracks 18 and 19 are of different lengths to tracks 17 and 20. This length variation facilitates the use of a Wheatstone bridge arrangement, in the sensor.

The intermediate pads 12, 13, 14 and 15 are themselves connected by conducting tracks 17, 18, 19 and 20 to output pads 21, 22, 23 and 24, respectively.

Soldered to each output pad 21, 22, 23 and 24 are four wires 25, 26, 27 and 28 (a two wire version is also envisaged). Wires 25 and 26 are carried within a PTFE cable sleeve 29 and wires 27 and 28 are carried within a second cable sleeve 30. The pads, 12-15, 21 to 24 and tracks 17 to 20 are copper, topped with gold, and are printed onto the FR4 substrate 4 in conventional manner.

The wires 25 to 28, within their sleeves 29, 30 pass under a clamp 31 of FR4 material which is glued to the substrate 4 along a line 32. It will be seen that the wires 25 to 28 sit in a hollowed out portion 33 of the substrate 4.

All wire wedge bonds are enclosed in an initial sealant, either Araldite 2014, at 60 deg. C., or Dymax 9001 (not separately shown). The connections for the wires 25 to 28, together with the PTFE cable sleeves 29 and 30, at feed-throughs 36, 37, are then enclosed in Raychem S1125 flexible epoxy (again, not separately shown). To enhance the seal between the PTFE sleeves 29, 30 and FR4 feed-throughs 36, 37 of the clamp 31, the sleeves are first etched with Tetra Etch and washed off, before the Raychem sealant is applied.

The connections of the wires 25 to 28 to the output pads 21 to 24 are made by soldering and are then coated with M-Coat-D acrylic (not separately shown).

The Raychem S1125 may be brushed on or injection moulded over all the connections and over the FR4 board. This sealant then forms an interface to which PR2001B2 aircraft sealant can be injection moulded. PR2001B2 will not seal well to the FR4 or to the PTFE and so the Raychem provides an effective intermediate structure to which the PR2001B2 will effectively seal. The PR2001B2 effectively acts as a potting compound for all the connections and an effective outer sealant for aircraft use.

Turning now to FIG. 2, this shows a side cutaway view of the sensor of FIG. 1 within an injection mould 38. The mould 38 comprises a bed 39 and first and second upper portions 40, 41. The bed 39 contains a hollowed out portion 42 into which is placed the FR4 board 4 with all the wires bonded and soldered into place and the clamp 31 attached. The application of the various sealants, as described above, to the wire connections may be made with the board 4 resting in the mould or before it is inserted.

Once all the wire connections and the feed-throughs have had initial sealant applied to them, the mould 38 is closed. The PTFE cable sleeves 29, 30 are sealed against the upper portion 41 of the mould in known manner. Aircraft sealant such as PR2001B2 is then injected under pressure into a cavity 45 of the mould through one or more injection ports 43. One or more outlet ports 44 may be connected to a vacuum source, to reduce the possibility of gas bubbles forming in the injected sealant by aiding complete filling of the mould cavity 45 with PR2001B2 sealant. It is preferred that the mould 38 is in fact placed in a vacuum chamber for the injection moulding step to be carried out there, as described above.

The invention claimed is:

1. A method of manufacturing a corrosion sensor, the corrosion sensor including a chip comprising a number of metallic strips mounted on a non-conducting substrate and a module for forming electrical connections to the strips whereby to enable communication between the strips and monitoring equipment for the sensor, the module including a number of wire connections, the method including the steps of manually coating at least some of the wire connections with a preliminary sealing compound and curing the preliminary sealing compound followed by encapsulating the wire connections within a flexible epoxy compound said flexible epoxy compound being a different compound than said preliminary sealing compound, and subsequently, encapsulating the flexible epoxy compound within a second sealing compound of aircraft sealant by an injection moulding process, said aircraft sealant having a service temperature range of between −62° C. and 216° C.

2. A method according to claim 1, in which the step of encapsulating the wire connections within a flexible epoxy compound is made by an injection moulding step.

3. A method according to claim 1, in which the first and second wire connections are made at pads on the chip and at a set of intermediate pads in the module, respectively, by ultrasonically bonding very fine wires, at first ends thereof, to the chip pads and, at second ends thereof, to the intermediate pads.

4. A method according to claim 1, wherein output wires from the sensor are attached to output pads and then clamped in position to the module with a clamp.

5. A method according to claim 4, wherein the clamp defines feed-through passages for the output wires and the flexible epoxy compound is applied to the feed-through passages.

6. A method according to claim 5, wherein the output wires have PTFE sleeves and the method includes the step of etching the PTFE sleeves with an etching product.

7. A method according to claim 1, in which the mould for an injection moulding process is connectible to a vacuum source at an outlet therefrom.

8. A method according to claim 7, in which the step of connecting said mould outlet to a vacuum source comprises placing the injection mould in a vacuum chamber thereby to connect any mould outlets to the vacuum within the vacuum chamber.

9. A method according to claim 1, including the step of supplying the flexible epoxy compound to an injection mould, for the injection moulding step, in a manufacturer-supplied air-tight container.

10. A method according to claim 9, in which the air-tight container comprises an evacuated tube.

11. A method according to claim 9, in which the injection moulding step is carried out by connecting the air-tight container to a mould inlet and forcing the sealing compound from the air-tight container into the mould.

12. A method according to claim 9, in which the airtight container comprises an evacuated tube and in which the step of forcing the sealing compound from the tube comprises compressing part of the tube whereby to reduce the volume inside the tube.

13. A corrosion sensor including a number of metallic strips mounted on a non-conducting substrate and a module for forming electrical connections to the strips whereby to enable communication between the strips and monitoring equipment for the sensor, the module including a number of wire connections the wire connections being encapsulated within a flexible epoxy compound and the flexible epoxy compound being encapsulated within an injection moulded second sealing compound of aircraft sealant having a service temperature range of between −62° C. and 216° C. and said epoxy compound being a different compound from said second sealing compound.

14. A corrosion sensor manufactured according to the method of claim 1.

* * * * *